(12) United States Patent
Baril et al.

(10) Patent No.: US 12,059,176 B2
(45) Date of Patent: Aug. 13, 2024

(54) SURGICAL ACCESS DEVICE WITH DIFFERENTIAL PRESSURE INDUCED FLUID EVACUATION

(71) Applicant: Covidien LP, Mansfield, MA (US)

(72) Inventors: Jacob C. Baril, Norwalk, CT (US); Garrett P. Ebersole, Hamden, CT (US); Justin Thomas, New Haven, CT (US); Saumya Banerjee, Hamden, CT (US); Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 588 days.

(21) Appl. No.: 17/063,582

(22) Filed: Oct. 5, 2020

(65) Prior Publication Data
US 2022/0104848 A1    Apr. 7, 2022

(51) Int. Cl.
*A61B 17/34*    (2006.01)
(52) U.S. Cl.
CPC ...... *A61B 17/3462* (2013.01); *A61B 17/3423* (2013.01); *A61B 17/3474* (2013.01); *A61B 17/3498* (2013.01); *A61B 2017/3464* (2013.01); *A61B 2217/005* (2013.01)
(58) Field of Classification Search
CPC ............ A61B 17/3462; A61B 17/3423; A61B 17/3474; A61B 17/3498; A61B 2217/005
See application file for complete search history.

(56) References Cited

U.S. PATENT DOCUMENTS

| | | |
|---|---|---|
| 397,060 A | 1/1889 | Knapp |
| 512,456 A | 1/1894 | Sadikova |
| 1,213,005 A | 1/1917 | Pillsbury |
| 2,912,981 A | 11/1959 | Keough |
| 2,936,760 A | 5/1960 | Gains |
| 3,039,468 A | 6/1962 | Price |
| 3,050,066 A | 8/1962 | Koehn |
| 3,253,594 A | 5/1966 | Matthews et al. |
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |

(Continued)

FOREIGN PATENT DOCUMENTS

| | | |
|---|---|---|
| EP | 0480653 A1 | 4/1992 |
| EP | 0610099 A2 | 8/1994 |

(Continued)

*Primary Examiner* — Shaun L David
*Assistant Examiner* — Brigid K Byrd
(74) *Attorney, Agent, or Firm* — Draft Masters PLLC

(57) ABSTRACT

A surgical access device includes a tube and a housing coupled to the tube. The housing is configured for passage of a surgical instrument therethrough. The housing includes first and second chambers where the second chamber surrounds the first chamber. A seal is disposed in the first chamber. A port extends from the housing and is in fluid communication with the second chamber. A nozzle is defined between a distal portion of an outer wall of the first chamber and a wall of the housing. The nozzle is configured to direct fluid towards the second chamber.

18 Claims, 4 Drawing Sheets

(56) References Cited

U.S. PATENT DOCUMENTS

| | | | |
|---|---|---|---|
| 3,961,632 A | 6/1976 | Moossun | |
| RE29,207 E | 5/1977 | Bolduc et al. | |
| 4,083,369 A | 4/1978 | Sinnreich | |
| 4,217,889 A | 8/1980 | Radovan et al. | |
| 4,243,050 A | 1/1981 | Littleford | |
| 4,276,874 A | 7/1981 | Wolvek et al. | |
| 4,312,353 A | 1/1982 | Shahbabian | |
| 4,327,709 A | 5/1982 | Hanson et al. | |
| 4,345,606 A | 8/1982 | Littleford | |
| 4,411,654 A | 10/1983 | Boarini et al. | |
| 4,416,267 A | 11/1983 | Garren et al. | |
| 4,490,137 A | 12/1984 | Moukheibir | |
| 4,496,345 A | 1/1985 | Hasson | |
| 4,574,806 A | 3/1986 | McCarthy | |
| 4,581,025 A | 4/1986 | Timmermans | |
| 4,596,554 A | 6/1986 | Dastgeer | |
| 4,596,559 A | 6/1986 | Fleischhacker | |
| 4,608,965 A | 9/1986 | Anspach, Jr. et al. | |
| 4,644,936 A | 2/1987 | Schiff | |
| 4,654,030 A | 3/1987 | Moll et al. | |
| 4,685,447 A | 8/1987 | Iversen et al. | |
| 4,701,163 A | 10/1987 | Parks | |
| 4,738,666 A | 4/1988 | Fuqua | |
| 4,769,038 A | 9/1988 | Bendavid et al. | |
| 4,772,266 A | 9/1988 | Groshong | |
| 4,779,611 A | 10/1988 | Grooters et al. | |
| 4,784,133 A | 11/1988 | Mackin | |
| 4,793,348 A | 12/1988 | Palmaz | |
| 4,798,205 A | 1/1989 | Bonomo et al. | |
| 4,800,901 A | 1/1989 | Rosenberg | |
| 4,802,479 A | 2/1989 | Haber et al. | |
| 4,813,429 A | 3/1989 | Eshel et al. | |
| 4,840,613 A | 6/1989 | Balbierz | |
| 4,854,316 A | 8/1989 | Davis | |
| 4,861,334 A | 8/1989 | Nawaz | |
| 4,865,593 A | 9/1989 | Ogawa et al. | |
| 4,869,717 A | 9/1989 | Adair | |
| 4,888,000 A | 12/1989 | McQuilkin et al. | |
| 4,899,747 A | 2/1990 | Garren et al. | |
| 4,917,668 A | 4/1990 | Haindl | |
| 4,931,042 A | 6/1990 | Holmes et al. | |
| 4,955,895 A | 9/1990 | Sugiyama et al. | |
| 5,002,557 A | 3/1991 | Hasson | |
| 5,009,643 A | 4/1991 | Reich et al. | |
| 5,030,206 A | 7/1991 | Lander | |
| 5,030,227 A | 7/1991 | Rosenbluth et al. | |
| 5,074,871 A | 12/1991 | Groshong | |
| 5,098,392 A | 3/1992 | Fleischhacker et al. | |
| 5,104,383 A | 4/1992 | Shichman | |
| 5,116,318 A | 5/1992 | Hillstead | |
| 5,116,357 A | 5/1992 | Eberbach | |
| 5,122,122 A | 6/1992 | Allgood | |
| 5,122,155 A | 6/1992 | Eberbach | |
| 5,137,512 A | 8/1992 | Burns et al. | |
| 5,141,494 A | 8/1992 | Danforth et al. | |
| 5,141,515 A | 8/1992 | Eberbach | |
| 5,147,302 A | 9/1992 | Euteneuer et al. | |
| 5,147,316 A | 9/1992 | Castillenti | |
| 5,147,374 A | 9/1992 | Fernandez | |
| 5,158,545 A | 10/1992 | Trudell et al. | |
| 5,159,925 A | 11/1992 | Neuwirth et al. | |
| 5,163,949 A | 11/1992 | Bonutti | |
| 5,176,692 A | 1/1993 | Wilk et al. | |
| 5,176,697 A | 1/1993 | Hasson et al. | |
| 5,183,463 A | 2/1993 | Debbas | |
| 5,188,596 A | 2/1993 | Condon et al. | |
| 5,188,630 A | 2/1993 | Christoudias | |
| 5,195,507 A | 3/1993 | Bilweis | |
| 5,201,742 A | 4/1993 | Hasson | |
| 5,201,754 A | 4/1993 | Crittenden et al. | |
| 5,209,725 A | 5/1993 | Roth | |
| 5,215,526 A | 6/1993 | Deniega et al. | |
| 5,222,970 A | 6/1993 | Reeves | |
| 5,226,890 A | 7/1993 | Ianniruberto et al. | |
| 5,232,446 A | 8/1993 | Arney | |
| 5,232,451 A | 8/1993 | Freitas et al. | |
| 5,234,454 A | 8/1993 | Bangs | |
| 5,250,025 A | 10/1993 | Sosnowski et al. | |
| 5,258,026 A | 11/1993 | Johnson et al. | |
| 5,269,753 A | 12/1993 | Wilk | |
| 5,290,249 A | 3/1994 | Foster et al. | |
| 5,308,327 A | 5/1994 | Heaven et al. | |
| 5,309,896 A | 5/1994 | Moll et al. | |
| 5,314,443 A | 5/1994 | Rudnick | |
| 5,318,012 A | 6/1994 | Wilk | |
| 5,330,497 A | 7/1994 | Freitas et al. | |
| 5,342,307 A | 8/1994 | Euteneuer et al. | |
| 5,346,504 A | 9/1994 | Ortiz et al. | |
| 5,359,995 A | 11/1994 | Sewell, Jr. | |
| 5,361,752 A | 11/1994 | Moll et al. | |
| 5,370,134 A | 12/1994 | Chin et al. | |
| 5,383,889 A | 1/1995 | Warner et al. | |
| 5,397,311 A | 3/1995 | Walker et al. | |
| 5,402,772 A | 4/1995 | Moll et al. | |
| 5,407,433 A | 4/1995 | Loomas | |
| 5,431,173 A | 7/1995 | Chin et al. | |
| 5,445,615 A | 8/1995 | Yoon | |
| 5,468,248 A | 11/1995 | Chin et al. | |
| 5,514,091 A | 5/1996 | Yoon | |
| 5,514,153 A | 5/1996 | Bonutti | |
| 5,540,658 A | 7/1996 | Evans et al. | |
| 5,540,711 A | 7/1996 | Kieturakis et al. | |
| 5,607,441 A | 3/1997 | Sierocuk et al. | |
| 5,607,443 A | 3/1997 | Kieturakis et al. | |
| 5,632,761 A | 5/1997 | Smith et al. | |
| 5,656,013 A | 8/1997 | Yoon | |
| 5,667,479 A | 9/1997 | Kieturakis | |
| 5,667,520 A | 9/1997 | Bonutti | |
| 5,704,372 A | 1/1998 | Moll et al. | |
| 5,707,382 A | 1/1998 | Sierocuk et al. | |
| 5,713,869 A | 2/1998 | Morejon | |
| 5,722,986 A | 3/1998 | Smith et al. | |
| 5,728,119 A | 3/1998 | Smith et al. | |
| 5,730,748 A | 3/1998 | Fogarty et al. | |
| 5,730,756 A | 3/1998 | Kieturakis et al. | |
| 5,738,628 A | 4/1998 | Sierocuk et al. | |
| 5,755,693 A | 5/1998 | Walker et al. | |
| 5,762,604 A | 6/1998 | Kieturakis | |
| 5,772,680 A | 6/1998 | Kieturakis et al. | |
| 5,779,728 A | 7/1998 | Lunsford et al. | |
| 5,797,947 A | 8/1998 | Mollenauer | |
| 5,803,901 A | 9/1998 | Chin et al. | |
| 5,810,867 A | 9/1998 | Zarbatany et al. | |
| 5,814,060 A | 9/1998 | Fogarty et al. | |
| 5,836,913 A | 11/1998 | Orth et al. | |
| 5,836,961 A | 11/1998 | Kieturakis et al. | |
| 5,865,802 A | 2/1999 | Yoon et al. | |
| 5,893,866 A | 4/1999 | Hermann et al. | |
| 5,925,058 A | 7/1999 | Smith et al. | |
| 6,361,543 B1 | 3/2002 | Chin et al. | |
| 6,368,337 B1 | 4/2002 | Kieturakis et al. | |
| 6,375,665 B1 | 4/2002 | Nash et al. | |
| 6,379,372 B1 | 4/2002 | Dehdashtian et al. | |
| 6,432,121 B1 | 8/2002 | Jervis | |
| 6,447,529 B2 | 9/2002 | Fogarty et al. | |
| 6,468,205 B1 | 10/2002 | Mollenauer et al. | |
| 6,506,200 B1 | 1/2003 | Chin | |
| 6,514,272 B1 | 2/2003 | Kieturakis et al. | |
| 6,517,514 B1 | 2/2003 | Campbell | |
| 6,527,787 B1 | 3/2003 | Fogarty et al. | |
| 6,540,764 B1 | 4/2003 | Kieturakis et al. | |
| 6,796,960 B2 | 9/2004 | Cioanta et al. | |
| 8,454,645 B2 | 6/2013 | Criscuolo et al. | |
| 8,551,049 B2 * | 10/2013 | Ott | A61B 17/3421 |
| | | | 604/167.03 |
| 8,551,050 B2 | 10/2013 | Ott et al. | |
| 8,795,223 B2 | 8/2014 | Stearns et al. | |
| 2002/0128603 A1 * | 9/2002 | Booth | A61B 17/3421 |
| | | | 604/164.01 |
| 2007/0088275 A1 * | 4/2007 | Stearns | A61M 13/003 |
| | | | 604/164.01 |
| 2016/0158468 A1 | 6/2016 | Tang et al. | |
| 2017/0007295 A1 * | 1/2017 | Geisz | A61B 17/3421 |
| 2021/0267639 A1 * | 9/2021 | Fischer | A61M 13/003 |

(56) References Cited

U.S. PATENT DOCUMENTS

FOREIGN PATENT DOCUMENTS

| | | | |
|---|---|---|---|
| EP | 0880939 | A1 | 12/1998 |
| WO | 9206638 | A1 | 4/1992 |
| WO | 9218056 | A1 | 10/1992 |
| WO | 9221293 | A1 | 12/1992 |
| WO | 9221295 | A1 | 12/1992 |
| WO | 9309722 | A1 | 5/1993 |
| WO | 9721461 | A1 | 6/1997 |
| WO | 9912602 | A1 | 3/1999 |
| WO | 0126724 | A2 | 4/2001 |
| WO | 02096307 | A2 | 12/2002 |
| WO | 2004032756 | A2 | 4/2004 |
| WO | 2017184876 | A1 | 10/2017 |
| WO | 2020036497 | A1 | 2/2020 |

* cited by examiner

SURGICAL ACCESS DEVICE WITH DIFFERENTIAL PRESSURE INDUCED FLUID EVACUATION

FIELD

The present disclosure is generally related to devices for accessing a surgical site. More particularly, this disclosure relates to a surgical access device with differential pressure induced fluid evacuation.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula) is introduced through an opening in tissue (i.e., a naturally occurring orifice or an incision) to provide access to an underlying surgical site in the body. The incision is typically made using an obturator having a blunt or sharp tip that has been inserted within the passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall and is then removed to permit introduction of additional surgical instrumentation through the surgical access device to perform the surgical procedure.

In minimally invasive surgery, the use of electro-surgical instruments to cut or otherwise treat tissues at times generates harmful and contaminated byproducts including smoke, aerosols, vapor, mist, etc., that compromise the field of view of surgeons or medical staff. As surgical instruments are exchanged with one another in the surgical access device, the harmful and contaminated byproducts may exit the surgical site through the access device exposing the medical staff to the gases, smoke, vapors, aerosols, etc. During these procedures, it may be challenging to minimize smoke (including gas and other particulates) that escapes from the pressurized body cavity when one instrument is removed from the surgical access device and prior to the introduction of another surgical device through the surgical access device, for instance. In some surgeries, a dedicated surgical access device may be configured to couple to a source of vacuum and remove the harmful fluids from the surgical site and away from the medical staff. Other surgical access devices may have separate channels, lumens, or tubes for filtering and removing harmful or contaminated fluids from the surgical site. A surgical access device that passively removes contaminated fluids from the field of view of, and away from, the medical staff is desired. The present disclosure presents a surgical access device that rapidly and effectively removes fluids from a surgical site while also providing necessary insufflation fluid to maintain a proper surgical site in a body.

SUMMARY

This disclosure generally relates to a surgical access device including a tube defining a lumen and a housing coupled to a proximal portion of the tube. The housing is configured for passage of a surgical instrument therethrough. The housing includes a first chamber axially aligned with the lumen of the tube. A second chamber is defined between an outer wall of the first chamber and an inner wall of the housing, the second chamber surrounding the first chamber. A seal is disposed in the first chamber. A port extends from the housing and is in fluid communication with the second chamber. The port is configured to be coupled to a source of vacuum. A distal portion of the outer wall of the first chamber and a wall of the housing define a nozzle that is in fluid communication with the lumen of the tube. The nozzle is configured to direct a proximally flowing fluid towards the second chamber.

In aspects, the nozzle may be disposed distally of the seal.

In yet another aspect, distalmost portions of the first chamber and the wall of the housing may form a convergent nozzle section of the nozzle, and the walls of the housing and the second chamber may form a divergent nozzle section of the nozzle.

In a further aspect, the nozzle may include a throat pressure that is less than a first chamber pressure of the first chamber and a second chamber pressure of the second chamber.

In an additional aspect, the second chamber pressure may be less than the first chamber pressure thereby defining a differential pressure such that proximally flowing fluid may be directed into the second chamber.

In another aspect, the second chamber may have a pressure that is less than a pressure of the first chamber thus defining a differential pressure, such that when the fluid is flowing in a proximal direction, the fluid flows into the second chamber due to the differential pressure.

In aspects, the housing may include a port, and fluid in the nozzle exits the surgical access device via tubing coupled to the port.

In additional aspects, the housing may further include a duckbill valve and the nozzle is disposed distally of the duckbill valve and the seal.

In yet other aspects, the opening of the first chamber may have a diameter that is approximately equal to a diameter of the lumen.

In other aspects, the surgical access device may further include an input port, an output port, and a passage fluidly coupling the input and output ports, wherein fluid introduced into the input port is delivered to a working space via the output port.

In a further aspect, the passage may be disposed between inner and outer walls of the tube.

In accordance with another aspect of this disclosure, a housing assembly for a surgical access device includes a seal assembly having a seal. A housing is coupled to the seal assembly. The housing includes a first chamber and a second chamber. The second chamber is defined between an outer surface of the first chamber and an inner surface of the housing. The housing also has a nozzle disposed distally of the seal. The nozzle is defined between a distal portion of the first chamber and the inner surface of the housing. The nozzle is configured to direct fluid into the second chamber.

In aspects, distalmost portions of the first chamber and the wall of the housing may form a convergent nozzle section of the nozzle. The walls of the housing and the second chamber may form a divergent nozzle section of the nozzle.

In an aspect, the second chamber may have a second chamber pressure that is less than a first chamber pressure thereby defining a differential pressure such that fluid flowing towards the seal assembly may be directed through the nozzle and into the second chamber due to the differential pressure.

In another aspect, the seal assembly may include an evacuation port in fluid communication with the second chamber, the evacuation port configured to be coupled to a source of vacuum.

In further aspects, the housing assembly may include an insufflation fluid port coupled to the housing. The insufflation fluid port may be configured to allow an insufflation fluid to be introduced into a surgical working space in a body.

In yet even further aspects, an evacuation port is coupled to the housing, wherein the evacuation port is in fluid communication with the second chamber to permit fluid flowing into the second chamber to be evacuated from the housing.

In an aspect, the housing may be coupled to a tube, the tube configured to permit insertion and removal of a surgical instrument into a surgical working space.

In particular aspects, the first chamber may have a pressure that is greater than a pressure of the second chamber, thereby defining a differential pressure that directs fluid flow into the second chamber.

In an additional aspect, the first chamber may include an orifice at a distal portion thereof, the orifice spaced apart from a distal portion of walls of the housing thereby forming at least a portion of the nozzle. The orifice may be axially aligned with a tube coupled to the housing and may include a diameter approximately equal to a diameter of the tube.

The details of one or more aspects of the disclosure are set forth in the accompanying drawings and the description below. Other features, objects, and advantages of the surgical access device described in this disclosure will be apparent from the description and drawings, and from the claims.

DESCRIPTION OF DRAWINGS

The accompanying drawings, which are incorporated in and constitute a part of this specification, illustrate aspects and features of the disclosure and, together with the detailed description below, serve to further explain the disclosure, in which.

Figure 1:
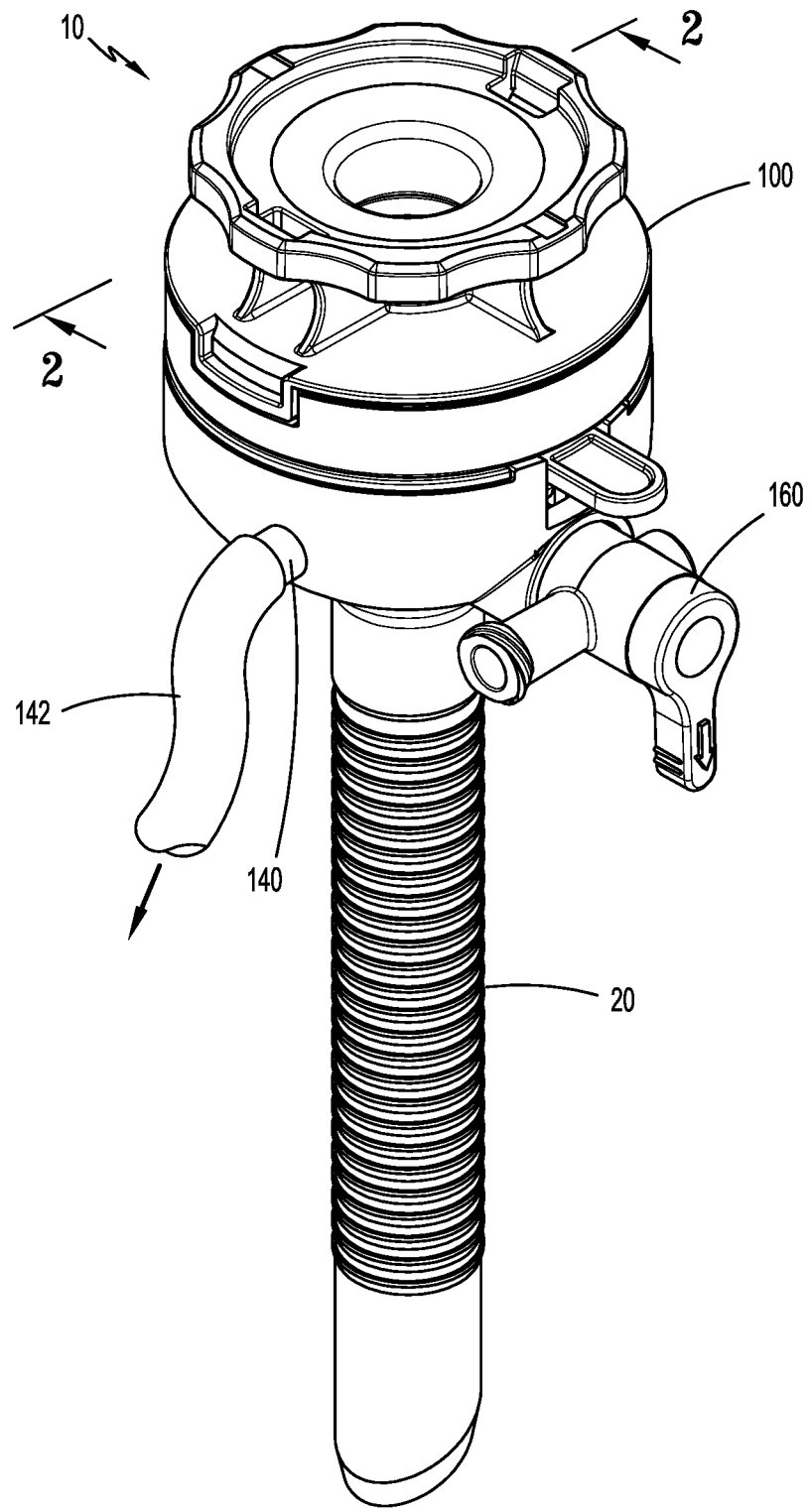
FIG. 1 is a perspective view of a surgical access device including a seal assembly, a housing with an evacuation port and an insufflation port, and a tube extending from the housing.

Further details and various aspects of this disclosure are described in more detail below with reference to the appended figures.

DETAILED DESCRIPTION

Aspects of the presently disclosed surgical access devices are described in detail with reference to the drawings, in which like reference numerals designate identical or corresponding elements in each of the several views. However, it is to be understood that the disclosed devices are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Descriptions of technical features of an illustrative surgical access device with fluid evacuation induced by a differential pressure in accordance with the disclosure should typically be considered as available and applicable to other similar features of another device of the disclosure. Accordingly, technical features described herein in connection with one illustrative surgical access device may apply to other devices of the disclosure, and thus duplicative descriptions may be omitted herein.

As used herein the term "distal" refers to that portion of the surgical access device, or component thereof, farther from the user, while the term "proximal" refers to that portion of the surgical access device, or component thereof, closer to the user.

This disclosure relates to a surgical access device configured to passively direct fluid, gas, and/or vapor out of and away from a surgical working space to maintain a clear field of vision and maintain a safe operating room environment for the surgeons and medical staff. Often, smoke or contaminated vapors may be generated by surgical instruments during surgery, and with the removal and insertion of surgical instruments through a surgical access device, the smoke or contaminated vapors may escape into the operating room or blur the field of vision of a surgeon or other medical staff.

With reference to FIG. 1, a surgical access device 10 having a tube 20 and a housing 100 is illustrated. The housing 100 includes a fluid evacuation port 140. The surgical access device 10 may be positioned by a medical professional through an opening in a body to create access to a surgical working space. The surgical access device 10 is configured to permit the removal and insertion of a surgical instrument into the working space while also evacuating smoke, vapor, gas, or other fluids from the surgical working space. In aspects, an insufflation fluid may be supplied to a surgical working space via an insufflation port 160 that is in fluid communication with a lumen 22 (FIG. 2) of the tube 20. An evacuation port 140 may be coupled to a source of vacuum (not shown) using tubing 142 to remove fluid from the housing 100.

Figure 2:
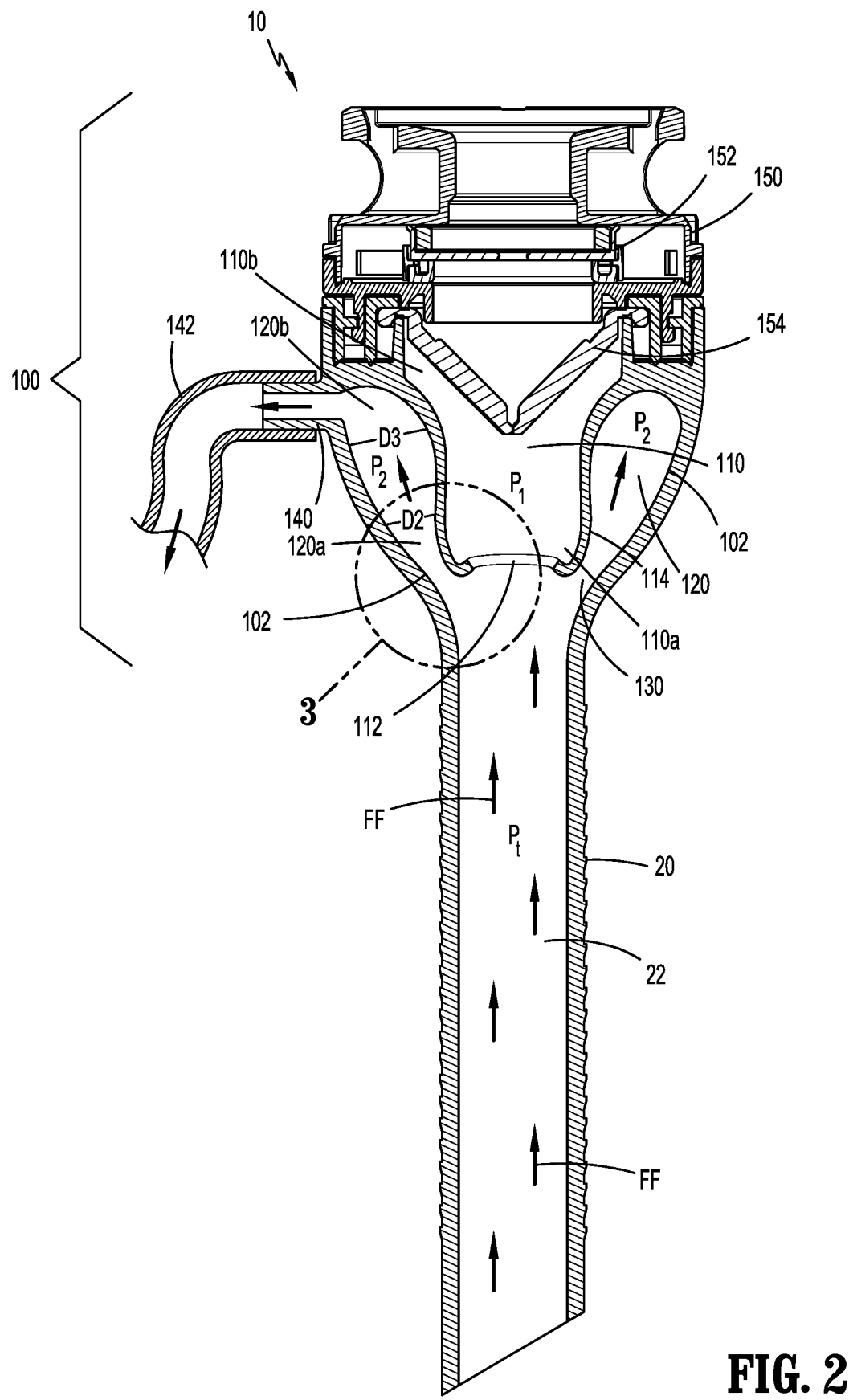
FIG. 2 is a side cross-sectional view of the surgical access device of FIG. 1 taken along section line 2-2 illustrating the housing with a first chamber, a second chamber, a nozzle, and the evacuation port.

With reference to FIG. 2, the housing 100 of the surgical access device 10 includes a first chamber 110, a second chamber 120, a nozzle 130 defined between the first chamber 110 and the second chamber 120, the evacuation port 140, and a seal assembly 150. The housing 100 is in fluid communication with the lumen 22 of the tube 20. The second chamber 120 surrounds the first chamber 110 and is defined between a wall 114 of the first chamber 110 and a wall 102 of the housing 100. The nozzle 130 separates a distal portion of the first chamber 110 and a distal portion of the second chamber 120. The nozzle 130 is in fluid communication with the lumen 22 of the tube 20 and with the second chamber 120. The nozzle 130 is configured to direct fluid into the second chamber 120 and away from the first chamber 110, such that a fluid (e.g., smoke or contaminated vapor) flowing proximally in the tube 20 is directed into the second chamber 120. The evacuation port 140 is in fluid communication with the second chamber 120. The seal assembly 150 is coupled to a proximal portion of the housing 100. In aspects, the seal assembly 150 includes an instrument seal 152 and a duckbill valve or duckbill seal 154. The duckbill seal 154 extends distally into the first chamber 110. The nozzle 130 is disposed distally of the duckbill seal 154 of the seal assembly 150. The insufflation port 160 (see FIG. 1) provides an insufflation fluid through the lumen 22, and thus maintains pressure in the surgical working space.

An opening at a distal portion of the first chamber 110 defines an orifice 112. The orifice 112 is concentric with the tube 20 and has a diameter approximately equal to the diameter of the tube 20. The orifice 112 and the wall 114 of the first chamber 110 are approximately collinear with the tube 20. In aspects, the wall 114 of the first chamber 110 is collinear with the tube 20 at a distal portion 110a of the first chamber 110, and not collinear with the tube 20 at a proximal portion 110b of the first chamber 110. The wall 114 of the distal portion 110a of the first chamber 110 and the wall 102 of the housing 100 near a distal portion 120a of the second chamber 120 are spaced apart from one another to define the nozzle 130. The orifice 112 is approximately adjacent to a distal portion of the nozzle 130. In aspects, the orifice 112 is approximately adjacent to a throat 132 of the nozzle 130 (FIG. 3).

Figure 3:
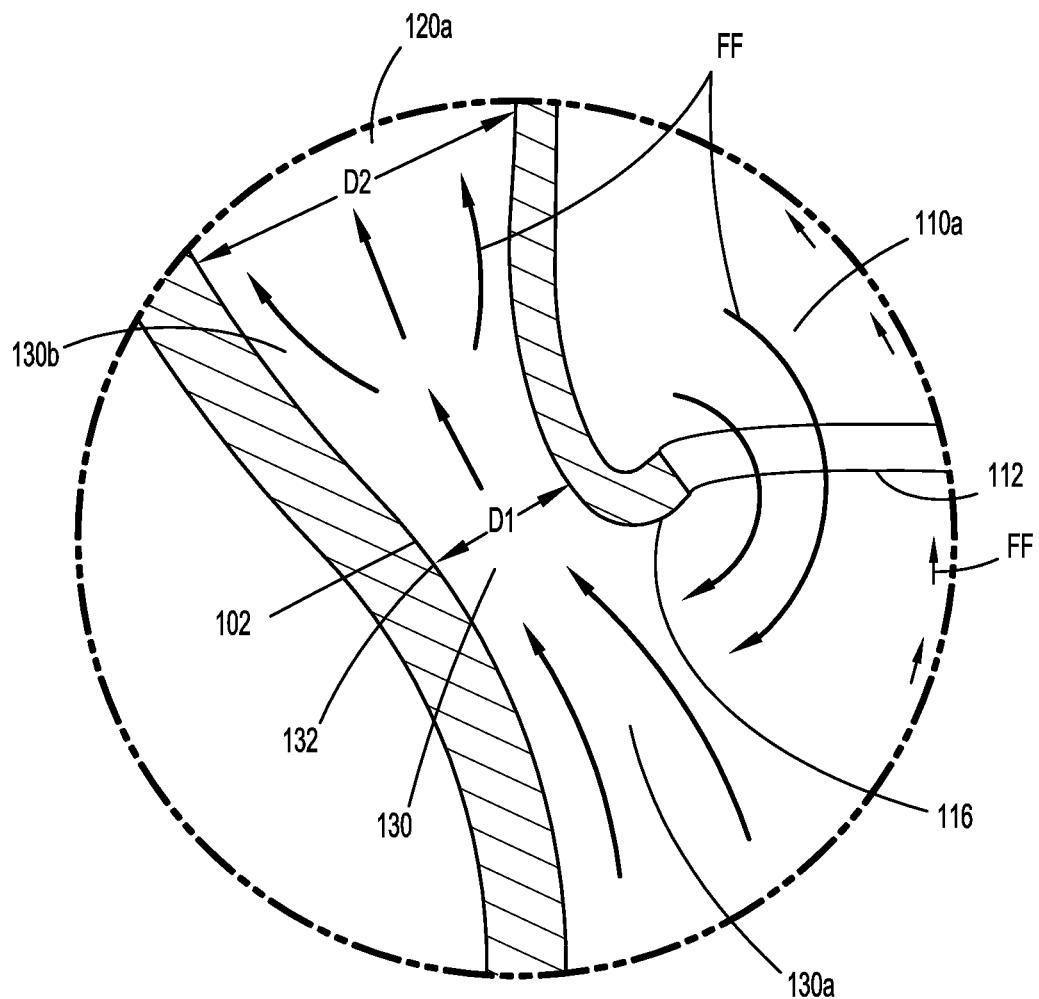
FIG. 3 is an enlarged view of the area of detail of FIG. 2 illustrating a flow path through and around the nozzle.

With additional reference to FIG. 3, the nozzle 130 may be a convergent-divergent (CD) nozzle 130. In a CD nozzle, such as CD nozzle 130, fluid initially flows into a continuously convergent section 130a such that the diameter of the nozzle 130, and therefore the cross-sectional area of the nozzle 130, constricts until it reaches its minimum chosen diameter or the minimum cross-sectional area commonly called the throat 132 of the nozzle 130. After the throat 132, the nozzle 130 begins to diverge, or the diameter, and therefore the cross-sectional area, continuously enlarges in a divergent section 130b. As dictated by the principles of conservation of mass and Bernoulli's equation, in the convergent section 130a, the flow is characterized by its change in velocity and pressure; as the fluid approaches the throat 132, the velocity of the fluid increases and the pressure decreases. As the fluid leaves the throat 132 and flows through the divergent section 130b, the velocity decreases and the pressure increases. Generally, in steady-state, incompressible flow with Mach numbers below 1, the highest velocity and lowest pressure of the fluid flow will occur at the throat 132. Additionally, in steady-state, incompressible flow, the upstream portion of the flow, or that entering the convergent section 130a of the nozzle 130, has a higher pressure than the downstream portion of the flow exiting the nozzle 130. Fluid normally flows in the direction of lower pressure, such that when presented with various paths of various pressures, more fluid will be pulled in the direction of the path with the lower pressure than the higher pressure.

In aspects, the nozzle 130 may be a Venturi nozzle 130. A Venturi nozzle operates in a manner similar to a CD nozzle. A Venturi nozzle 130 includes an elongated divergent section that is substantially longer than the convergent section and is configured to reduce pressure and energy loss at the nozzle exit. In aspects, the nozzle 130 is a divergent nozzle. In a divergent nozzle, the throat occurs at the very entrance of the nozzle, and the nozzle directs the flow into a wider area and introduces a pressure loss at the exit of the nozzle.

The wall 102 of the housing 100 at a distal portion thereof is connected to the tube 20. In aspects, the wall 102 of the housing 100 diverges from tube 20 which is approximately collinear with the wall 114 of the first chamber 110. The second chamber 120 is defined by the diverging wall 102 of the housing 100 and the wall 114 of the first chamber 110.

At a distal portion 120a of the second chamber 120, the second chamber 120 has a diameter D2, and at a proximal portion 120b of the second chamber 120, the second chamber 120 has a diameter D3 (FIG. 2). The diameters D2 and D3 are measured between the wall 102 of the housing 100 and the wall 114 of the first chamber 110. Between the distal portion 120a and the proximal portion 120b of the second chamber 120, the diameter of the second chamber 120 may continuously expand. Thus, the wall 102 of the housing 100 expands progressively outward from a distal-most portion thereof such that second chamber 120 is wider at proximal portions of the housing 100 than distal portions of the housing 100.

The distal portion 120a of the second chamber 120 further defines a proximal portion 130b of the nozzle 130. Additionally, the diameters D2 and D3 of the second chamber 120 are always larger than the smallest diameter D1 of the nozzle 130, which occurs at the throat 132 of the nozzle 130. Distal portion 130a of the nozzle 130 is defined by the wall 102 of the housing 100, a distal portion of the tube 20, and the wall 114 of the first chamber 110.

In aspects, the width of the second chamber 120 may be generally uniform throughout, but narrow at the distal portion 120a thereof that is near a proximal portion of the nozzle 130.

In aspects, the proximal-most portion of the second chamber 120 is positioned in the housing 100 distally of the seal assembly 150.

The second chamber 120 is in fluid communication with the evacuation port 140. The evacuation port 140 may be coupled to tubing 142. The tubing 142 may be connected to a source of vacuum (not shown). The evacuation port 140 is configured to remove fluid from the surgical access device 10 and away from the medical staff in an operating room. In aspects, the evacuated fluid may be filtered and/or contained downstream of the tubing 142. The evacuation port 140 may include a luer fitting. The tubing 142 provides a passage for the evacuated fluid to flow away from a surgeon or medical staff in an operating room.

The seal assembly 150 is disposed proximally of the first chamber 110 with the duckbill seal 154 extending into the first chamber 110. The seal assembly 150 opens into the first chamber 110 and is configured to accept the insertion of a surgical instrument therethrough. The seal assembly 150 is configured to inhibit fluid from escaping out of the housing 100 through the seal assembly 150 and into the environment.

With reference to FIGS. 2 and 3, as fluid flows through the tube 20 and into the housing 100, fluid pressure may build in the first chamber 110 relative to the second chamber 120. The first chamber 110 has a first pressure or first chamber pressure P1 and the second chamber has a second pressure or second chamber pressure P2, the difference between the pressures P1 and P2 defining a differential pressure.

The first chamber 110 is sealed off from the environment via the seal assembly 150, causing fluid flowing proximally into the first chamber 110 to slow down and become approximately stagnate. The fluid in the first chamber 110 has a static pressure that is approximately the same as the stagnation pressure since the fluid approximately stagnates and thus defines the first chamber pressure P1.

The second chamber 120 is open to the environment via the fluid evacuation port 140. Since the fluid is flowing through the second chamber 120, the second chamber 120 has a second chamber pressure P2 that is less than the first chamber pressure P1. Additionally, when the evacuation port 140, and therefore the second chamber 120, is coupled to a source of vacuum the second chamber pressure P2 will be further reduced relative to the first chamber pressure P1. The throat 132 of the nozzle 130 has a throat pressure that is about as small or smaller than either of the first chamber pressure P1 and the second chamber pressure P2.

Since the convergent section 130a of the nozzle 130 is open to the lumen 22 of the tube 20, the fluid entering the nozzle 130 will have the same pressure as the fluid flowing into the first chamber 110. However, as is typical of a nozzle as explained above, as the nozzle 130 converges, the pressure of the fluid flowing through the nozzle 130 drops. Fluid flowing into the first chamber 110 is met by the first chamber pressure P1. Additionally, since the second chamber 120 has a second chamber pressure P2 that is lower than the first chamber pressure P1 of the first chamber 110, thereby defining the differential pressure, the fluid will be encouraged to flow along the path with lower pressure (i.e., the path of least resistance). Thus, fluids are encouraged to flow into the lower pressure areas of the second chamber 120 and the nozzle 130 as opposed to the higher pressure areas of the first chamber 110.

With continued reference to FIG. 3, the nozzle 130 operates by directing fluid, as indicated by arrows "FF" in the tube to flow into the second chamber 120 and away from the orifice 112 of the first chamber 110. In aspects, the orifice 112 has an inward curved lip 116 such that fluid inside the first chamber 110 is encouraged to flow around the lip 116 of the orifice 112 and into the second chamber 120. Due to the no-slip condition and the lower pressure of the second chamber 120 and nozzle 130 relative to the first chamber 110, the fluid in the distal portion 110a of the first chamber 110 will be pulled around the lip 116.

According to the no-slip condition, a fluid at a surface has the same velocity of the surface creating a sharp velocity gradient that forms the basis of viscous shear flow. Fluid adjacent the fluid at the surface is affected by shear stress up until a boundary layer at which point the fluid is no longer affected by the shear stress exerted by the fluid at the surface. The shear stress acting on the fluid plays a role in the behavior of a fluid near a surface, including its velocity and flow path. Thus, a fluid may follow a surface, such as the lip 116.

The curvature of the lip 116 may be configured to reduce fluid eddies and stagnation in the first chamber 110 so that fluid in the first chamber 110 may more easily be pulled into the nozzle 130 around the lip 116. The lip 116 of the orifice 112 is configured to further define a convergent section 130a of the nozzle 130 between the lip 116 and the wall 102 of the housing 100. Most of the fluid will flow into the nozzle 130 as indicated by larger arrows FF, while some of the fluid will flow into the first chamber 110 as indicated by smaller arrows FF.

Referring again to FIG. 2, the fluid flows through the tube 20 and has a tube pressure Pt in the tube 20. At a proximal portion of the tube 20 that is in fluid communication with a distal portion of the housing 100, the lower pressure P2 of the second chamber 120 draws the fluid through the nozzle 130 and away from the first chamber 110 and orifice 112. In aspects, a source of vacuum coupled to the fluid evacuation port 140 further lowers the second chamber pressure P2 of the second chamber 120, and thus the fluid may flow faster through the nozzle 130 and into the second chamber 120. In aspects, the evacuation port 140 is coupled to the second chamber 120 within the housing 100 distally of the seal assembly 150.

The tube pressure Pt may be equal to or less than the first chamber pressure P1 of the first chamber 110.

Figure 4:
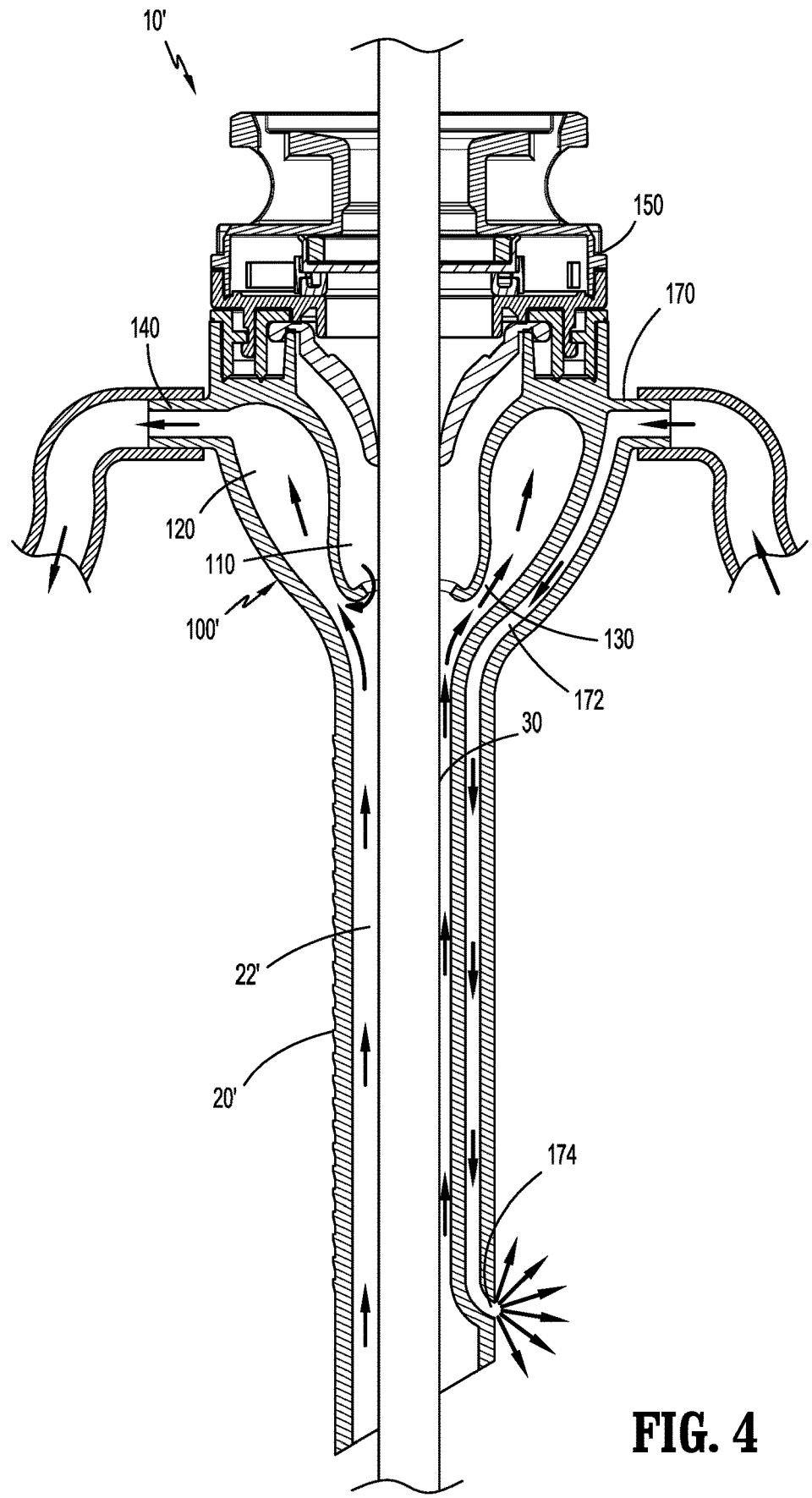
FIG. 4 is a side cross-sectional view of a surgical instrument inserted through a surgical access device having a housing, a seal assembly, a nozzle, an evacuation port, and an insufflation port, in accordance with another aspect of this disclosure.

When a surgical instrument 30 is inserted in the surgical access device 10, there is a gap between the surgical instrument 30 and tube 20' (see FIG. 4). The surgical instrument 30 forces the fluid to flow through the gap. As the fluid travels in the gap in the proximal direction it approaches the nozzle 130 and the orifice 120. The nozzle 130 guides the fluid to flow into the second chamber 120. Due to the differential pressure caused by the difference in pressure between the first chamber 110, the second chamber 120, and the nozzle 130, more fluid flows through nozzle 130 than the orifice 112 of the first chamber 110. In aspects, approximately all the fluid flows through the nozzle 130. Although illustrated with respect to FIG. 4, the same principles apply when the surgical instrument 30 is inserted through the tube 20 of the surgical access device 10.

When no surgical instrument is inserted in the surgical access device 10, fluid flows through the whole of the lumen 22 of the tube 20. The duckbill seal 154 inhibits the fluid flowing into and proximally out of the housing 100 via the chamber 110. Pressure builds in the first chamber 110 when the duckbill seal 154 is closed or the instrument seal 152 is sealed about a surgical instrument inserted therein. As the fluid travels proximally in the lumen 22 of the tube 20, it is drawn by the nozzle 130 into the second chamber 120. The fluid that traveled into the first chamber 110 is pulled back into the nozzle 130, as indicated in FIG. 3, due to the lower pressure of the nozzle 130 and second chamber 120. Thus, the surgical access device 10 may passively remove fluid from the surgical working space.

With reference to FIG. 4, a cross-sectional view of an alternate embodiment of a surgical access device is illustrated and identified as surgical access device 10'. The surgical access device 10' includes a housing 100', a tube 20', and the seal assembly 150. The housing 100' of the surgical access device 10' includes an input port 170. The input port 170 is in fluid communication with a passage 172 that is coupled to or a part of the tube 20'. An output port 174 is in fluid communication to an end of the passage 172 opposite the input port 170. An insufflation fluid may be supplied to the surgical working space via the input port 170, fluid passage, 172, and output port 174. Insufflation fluid is supplied to the working space to offset any loss of insufflation fluid or pressure in the working space caused by fluid flowing out of the surgical working space through the lumen 22' of the tube 20' via the nozzle 130, second chamber 120, and the evacuation port 140. In aspects, the input port 170 may include a luer fitting.

It should be understood that various aspects disclosed herein may be combined in different combinations than the combinations specifically presented in the description and accompanying drawings. It is envisioned that the elements and features may be combined with the elements and features of another without departing from the scope of the disclosure. As well, one skilled in the art will appreciate further features and advantages of the disclosure.

What is claimed is:
1. A surgical access device comprising:
   a tube defining a lumen; and
   a housing coupled to a proximal portion of the tube, the housing configured for passage of a surgical instrument through the housing, the housing having:
      a first chamber including a distal opening axially aligned with the lumen of the tube, the distal opening axially spaced from the tube along a longitudinal axis of the tube;

a second chamber defined between an outer wall of the first chamber and an inner wall of the housing, the second chamber circumferentially surrounding the first chamber;

a seal disposed in the first chamber;

an evacuation port extending from the housing and in fluid communication with the second chamber, the evacuation port configured to be coupled to a source of vacuum; and a nozzle including a convergent section, a divergent section, and a throat connecting the convergent section to the divergent section, the convergent section having a first diameter that is less than a diameter of the lumen, the throat having a second diameter that is less than the first diameter, the divergent section having a third diameter that is greater than the second diameter, the divergent section defined between a proximal portion of the outer wall of the first chamber and a proximal portion of the inner wall of the housing, the throat defined between a curved lip of the distal opening and a distal portion of the inner wall of the housing, the convergent section defined between a distal portion of the outer wall of the first chamber and an inner wall of the proximal portion of the tube, wherein the nozzle is configured to direct a proximally flowing fluid from the lumen towards the second chamber.

2. The surgical access device of claim 1, wherein the nozzle is disposed distally of the seal.

3. The surgical access device of claim 1, wherein the nozzle includes a throat pressure that is less than a first chamber pressure of the first chamber and a second chamber pressure of the second chamber.

4. The surgical access device of claim 3, wherein the second chamber pressure is less than the first chamber pressure thereby defining a differential pressure such that the proximally flowing fluid is directed into the second chamber.

5. The surgical access device of claim 1, wherein the second chamber has a pressure that is less than a pressure of the first chamber thus defining a differential pressure such that fluid flowing in a proximal direction flows into the second chamber due to the differential pressure.

6. The surgical access device of claim 1, wherein a fluid in the nozzle exits the surgical access device via tubing coupled to the evacuation port.

7. The surgical access device of claim 1, wherein the housing further includes a duckbill valve, the nozzle is disposed distally of the duckbill valve and the seal.

8. The surgical access device of claim 1, wherein the distal opening of the first chamber has a diameter that is approximately equal to a diameter of the lumen.

9. The surgical access device of claim 1, further including an input port, an output port, and a passage fluidly coupling the input port and the output port, wherein fluid introduced into the input port is delivered to a working space via the output port.

10. The surgical access device of claim 9, wherein the passage is disposed between the inner wall and an outer wall of the tube.

11. A housing assembly for a surgical access device comprising:

a seal assembly having a seal; and a housing coupled to the seal assembly, the housing including:

a tube having a proximal portion coupled to the housing;

a first chamber and a second chamber, the first chamber having a distal end spaced from the proximal portion of the tube along a longitudinal axis of the tube, the second chamber defined between an outer surface of the first chamber and an inner surface of the housing; and a nozzle disposed distally of the seal, the nozzle having a convergent section including a first diameter, a divergent section having a second diameter greater than the first diameter, and a throat having a third diameter that is less than the first diameter and the second diameter, the throat joining the convergent section and the divergent section, the convergent section defined between a distal portion of a wall of the first chamber and an inner wall of the proximal portion of the tube, the divergent section defined between a proximal portion of the first chamber and a proximal portion of the inner surface of the housing, the throat defined between a curved lip of the distal end of the first chamber and a distal portion of the inner surface of the housing, wherein the nozzle is configured to direct fluid into the second chamber.

12. The housing assembly of claim 11, wherein the second chamber has a second chamber pressure that is less than a first chamber pressure thereby defining a differential pressure such that fluid flowing towards the seal assembly is directed through the nozzle and into the second chamber due to the differential pressure.

13. The housing assembly of claim 12, further including an evacuation port in fluid communication with the second chamber, the evacuation port configured to be coupled to a source of vacuum.

14. The housing assembly of claim 11, further including an insufflation fluid port coupled to the housing, the insufflation fluid port configured to allow an insufflation fluid to be introduced into a surgical working space in a body.

15. The housing assembly of claim 11, further including an evacuation port coupled to the housing, wherein the evacuation port is in fluid communication with the second chamber to permit fluid flowing into the second chamber to be evacuated from the housing.

16. The housing assembly of claim 11, wherein the tube is configured to permit insertion and removal of a surgical instrument into a surgical working space.

17. The housing assembly of claim 11, wherein the first chamber has a pressure that is greater than a pressure of the second chamber, thereby defining a differential pressure that directs fluid flow into the second chamber.

18. The housing assembly of claim 11, wherein the first chamber includes an orifice at the distal end of the first chamber, the orifice spaced apart from a distal portion of walls of the housing and is axially aligned with the tube, the orifice having a diameter approximately equal to a diameter of the tube.

* * * * *